United States Patent [19]

Steiner et al.

[11] Patent Number: 4,575,508

[45] Date of Patent: Mar. 11, 1986

[54] 2-SUBSTITUTED 1-(3'-AMINOALKYL)-1,2,3,4-TETRAHYDRO-β-CARBOLINES, AND THEIR USE AS ANTIARRHYTHMIC AGENTS

[75] Inventors: Gerd Steiner, Kirchheim; Claus D. Mueller, Viernheim; Dieter Lenke, Ludwigshafen, all of Fed. Rep. of Germany

[73] Assignee: BASF Aktiengesellschaft, Ludwigshafen, Fed. Rep. of Germany

[21] Appl. No.: 520,600

[22] Filed: Aug. 5, 1983

[30] Foreign Application Priority Data

Aug. 5, 1982 [DE] Fed. Rep. of Germany ....... 3229214
Mar. 17, 1983 [DE] Fed. Rep. of Germany ....... 3309596

[51] Int. Cl.[4] .................... A61K 31/40; A61K 31/44; C07D 471/04
[52] U.S. Cl. .................... 514/292; 546/85; 546/86; 544/126; 544/361
[58] Field of Search .................... 546/85, 86; 544/126, 544/361; 514/292

[56] References Cited

U.S. PATENT DOCUMENTS 2,759,000 8/1956 Huebner et al. .................... 546/85
4,272,539 6/1981 Koletar et al. .................... 546/85

*Primary Examiner*—Henry R. Jiles
*Assistant Examiner*—J. Richter
*Attorney, Agent, or Firm*—Oblon, Fisher, Spivak, McClelland & Maier

[57] ABSTRACT

2-Substituted 1-(3'-aminoalkyl)-1,2,3,4-tetrahydro-β-carbolines of the formula

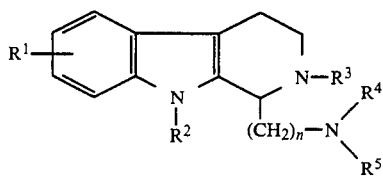

where n, $R^1$, $R^2$, $R^3$, $R^4$ and $R^5$ have the meanings given in the description, and their preparation and use.

The novel substances are useful for treating arrhythmia.

8 Claims, No Drawings

2-SUBSTITUTED 1-(3'-AMINOALKYL)-1,2,3,4-TETRAHYDRO-β-CARBOLINES, AND THEIR USE AS ANTIARRHYTHMIC AGENTS

The present invention relates to 2-substituted 1-(3'-aminoalkyl)-1,2,3,4-tetrahydro-β-carbolines, processes for their preparation and therapeutic agents containing these compounds and the use of these compounds in the treatment of disorders.

We have found that 2-substituted 1-(3'-aminoalkyl)-1,2,3,4-tetrahydro-β-carbolines of the formula I

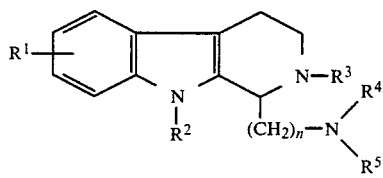

where n is an integer from 2 to 5, $R^1$ is hydrogen, halogen, trifluoromethyl, $C_1$–$C_4$-alkyl or $C_1$–$C_4$-alkoxy, $R^2$ is hydrogen, or $C_1$–$C_3$-alkyl, $R^3$ is $C_1$–$C_3$-acyl, $R^4$ is hydrogen or an alkyl or cycloalkyl radical of not more than 4 carbon atoms and $R^5$ is hydrogen or an alkyl or cycloalkyl radical of not more than 4 carbon atoms and, where $R^4$ is hydrogen, may furthermore be $C_1$–$C_4$-hydroxyalkyl or $C_2$–$C_4$-aminoalkyl in which the amine nitrogen atom can be substituted by $C_1$–$C_3$-alkyl or can form part of a 5-membered, 6-membered or 7-membered saturated ring which can contain another nitrogen atom or an oxygen atom as a further heteroatom, and any nitrogen atom present can be substituted by $C_1$–$C_3$-alkyl or $C_2$–$C_3$-hydroxyalkyl or by phenyl which is unsubstituted or monosubstituted by fluorine, chlorine, methoxy or methyl, or $R^4$ and $R^5$, together with the nitrogen atom, form a 5-membered, 6-membered or 7-membered saturated ring which can be substituted by one or more $C_1$–$C_3$-alkyl groups, a hydroxyl group and/or a phenyl group and can additionally contain nitrogen or oxygen as a further heteroatom, and any nitrogen atom present can be substituted by $C_1$–$C_3$-alkyl or $C_1$–$C_3$-hydroxyalkyl or by phenyl which is unsubstituted or monosubstituted by fluorine, chlorine, methoxy or methyl, and their salts with physiologically tolerated acids possess useful pharmacological properties.

$R^1$ is preferably hydrogen, methyl or chlorine, $R^2$ is preferably hydrogen, methyl or ethyl, $R^3$ is preferably $C_2$–$C_3$-acyl, in particular acetyl, and n is preferably 3.

The radical —$NR^4R^5$ is, in particular, dialkylamino or monoalkylamino, dialkylamino being preferred, but may furthermore be one of the following special heterocyclic structures: piperazine, piperidine or morpholine. A particularly suitable cycloalkyl radical is cyclopropyl.

The following compounds are particularly active: 1-[3'-(di-2-methylpropyl)-aminopropyl]-2-acetyl-9-methyl-1,2,3,4-tetrahydro-β-carboline, 1-(3'-dipropylaminopropyl)-2-acetyl-9-methyl-1,2,3,4-tetrahydro-β-carboline and 1-(3'-isopropyl-propylaminopropyl)-2-acetyl-9-methyl-1,2,3,4-tetrahydro-β-carboline.

Further examples include: 1-[3'-diisopropylaminopropyl]-2-acetyl-9-methyl-1,2,3,4-tetrahydro-β-carboline, 1-[3'-(di-2-butyl)-aminopropyl]-2-acetyl-9-methyl-1,2,3,4-tetrahydro-β-carboline, 1-[3'-(t-butyl)-aminopropyl]-2-acetyl-9-methyl-1,2,3,4-tetrahydro-β-carboline, 1-[3'-(isopropyl-2-methylpropyl)-aminopropyl]-2-acetyl-9-methyl-1,2,3,4-tetrahydro-β-carboline, 1-[3'-(di-n-butyl)-aminopropyl]-2-acetyl-9-methyl-1,2,3,4-tetrahydro-β-carboline, 1-[3'-(di-2-butyl)-aminopropyl]-2-acetyl-1,2,3,4-tetrahydro-β-carboline and 1-[3'-(di-n-butyl)-aminopropyl]-2-acetyl-1,2,3,4-tetrahydro-β-carboline.

The novel compounds of the formula I are prepared by a method wherein a compound of the formula II

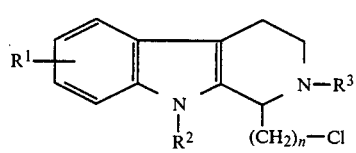

where n, $R^1$, $R^2$ and $R^3$ have the above meanings, is reacted with an amine of the formula $HNR^4R^5$ where $R^4$ and $R^5$ have the above meanings, and, if required, the resulting compound is converted to its salts with physiologically tolerated acids.

The reaction is advantageously carried out in the presence of one mole equivalent of a tertiary amine, eg. triethylamine, in an inert solvent, such as a saturated cyclic ether, in particular tetrahydrofuran or dioxane, or in a polar aprotic solvent, preferably dimethylformamide, at from 0° to 150° C., and is generally complete in the course of from 3 to 10 hours. The reaction may also be carried out in the presence of an excess of the amino alcohol III employed, the latter serving simultaneously as a solvent and as an acid acceptor.

In the majority of cases, the free compounds of the formula I are obtained in the form of crystals and can be recrystallized from a conventional organic solvent, preferably from a lower alcohol, eg. ethanol, or a lower ester, preferably ethyl acetate, or purified by column chromatography.

If desired, the novel compounds obtained are converted to an addition salt with a physiologically tolerated acid. Examples of conventional physiologically tolerated organic acids are oxalic acid, maleic acid, fumaric acid, lactic acid, tartaric acid, malic acid, citric acid, salicylic acid, adipic acid and benzoic acid, while examples of conventional physiologically tolerated inorganic acids are hydrochloric acid, hydrobromic acid or phosphoric acid and sulfuric acid. Other suitable acids are mentioned in, for example, J. Pharm. Sci. 66 (1977), 1.

As a rule, the addition salts with acids are obtained in a conventional manner, by mixing the free base or its solution with an appropriate acid or its solution in an organic solvent, for example a lower alcohol, such as methanol, ethanol or propanol, a lower ketone, such as acetone, methyl ethyl ketone or methyl isobutyl ketone, or an ether, such as diethyl ether, tetrahydrofuran or dioxane. To improve the deposition of crystals, it is also possible to use a mixture of the above solvents.

The starting compounds of the formula II are obtained, for example, by reacting a β-carboline derivative of the formula III

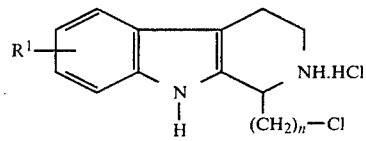

where n and $R^1$ have the above meanings, with an acylating agent $R^3$—Cl, where $R^3$ has the above meanings, under trapping conditions in the presence of a base, preferably pyridine, in an inert solvent, preferably dimethylformamide, while cooling, preferably at 0°–15° C.

Where $R^2$ in the desired end product is an alkyl radical, this is obtained by reacting the N-2-acyl compound with an alkyl chloride or dimethyl sulfate in an inert solvent.

The compounds III can be prepared by reacting the corresponding tryptamine derivative with an ω-haloaldehyde in a weakly acidic medium at from 50° to 100° C.

The novel compounds and their physiologically tolerated addition salts with acids possess useful pharmacological properties. They have a powerful antiarrhythmic action and are therefore particularly useful for the pharmacotherapy of cardiac arrhythmias.

To investigate the antiarrhythmic activity, the substances were administered orally to male Sprague-Dawley rats each weighing 200–250 g. 45 minutes later, the animals were anesthetized with sodium thiobutabarbital (100 mg/kg, administered intraperitoneally). Aconitine was used as the arrhythmogenic substance, and was infused intravenously 60 minutes after administration of the substance (dosage rate: 0.005 mg per kg per min.). In the case of untreated animals (N=52), the ECG showed arrhythmias after 2.74±0.07 min. The onset of these arrhythmias could be delayed by means of antiarrhythmics, the delay achieved being dose-dependent.

Linear relationships exist between the logarithms of the doses (mg/kg) of the test substances and the relative prolongation of the aconitine infusion duration (Δ%), from which relationships the dose which prolongs the infusion duration by 50% can be determined, as the ED 50%.

For further characterization of the substances, the dose at which the first cardiotoxic symptoms (changes in the initial ECG) or neurotoxic symptoms (coordination disturbances, convulsions, etc.) occurred was determined from the decimal-geometric dosage progression (factor $\sqrt[3]{10}$) used in the experiments. The quotient of the toxic dose and the antiarrhythmically effective dose (ED 50%) is a measure of the therapeutic index of the novel compounds.

The known antiarrhythmic quinidine was used as a comparative substance.

On aconitine-induced arrhythmia, the novel compounds (Table 1) are from 3 (Examples 21 and 4) to 59 times (Example 46) more effective than quinidine. Moreover, they possess a higher therapeutic index than quinidine. The toxic doses are from 12 (Example 42) to 23 times (Example 44) greater than the antiarrhythmically effective doses, whereas the corresponding ratio for quinidine is only 11.

TABLE 1

| Substance from Example No. | Antiarrhythmic action and toxicity, rat, oral administration | | | |
|---|---|---|---|---|
| | Aconitine-induced arrhythmia | | Toxicity | |
| | ED 50% (1) mg/kg | R.A. | Dose (3) mg/kg | Q (4) |
| 21 | 14.6 | 2.98 | 215 | 15 |
| 4 | 13.5 | 3.22 | 215 | 16 |
| 44 | 9.21 | 4.72 | 215 | 23 |
| 28 | 12.4 | 3.51 | 215 | 17 |
| 31 | 1.71 | 25.44 | 21.5 | 13 |
| 33 | 1.57 | 27.71 | 21.5 | 14 |
| 42 | 0.842 | 51.66 | 10 | 12 |
| 43 | 0.803 | 54.17 | 10 | 13 |
| 46 | 0.732 | 59.43 | 4.64 | 14 |
| quinidine | 43.5 | 1.00 | 215 | 11 |

(1) Dose (mg/kg) which prolongs the aconitine infusion duration by 50%.
(2) R.A. = relative activity, based on quinidine = 1.00.
(3) Dose (mg/kg) after the application of which the first toxic symptoms are observed.
(4) $Q = \frac{\text{Toxic dose (mg/kg)}}{\text{ED 50\% (mg/kg)}}$ The present invention therefore furthermore relates to drugs which contain a compound of the formula I or its physiologically tolerated addition salts with acids, and to the use of the novel compounds in the treatment of disorders.

The novel compounds can be used in the conventional solid or liquid pharmaceutical forms, such as tablets, film tablets, capsules, powders, granules, coated tablets, suppositories or solutions. These are prepared in a conventional manner, and to do this the active compounds are mixed with the conventional pharmaceutical assistants, such as tablet binders, fillers, preservatives, tablet disintegrators, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart, 1978). The forms for administration thus obtained usually contain the active compound in an amount of from 0.1 to 99% by weight.

The dosage of the novel compounds depends on the age, condition and weight of the patient and on the route of administration. As a rule, the daily dose of active compound is from 5 to 75 mg/kg in the case of oral administration and from 1 to 10 mg/kg in the case of parenteral administration.

The examples which follow illustrate the invention.

EXAMPLE 1

1-(3'-Dimethylaminopropyl)-2-acetyl-9-methyl-1,2,3,4-tetrahydro-β-carboline (a) Preparation of the starting material 1-(3'-chloropropyl)-2-acetyl-1,2,3,4-tetrahydro-β-carboline 17.1 g (60 millimoles) of 1-(3'-chloropropyl)-1,2,3,4-tetrahydro-β-carboline hydrochloride were dissolved in 240 ml of dimethylformamide while heating, and the solution was then cooled to 5° C. in an ice bath. 11.5 g (150 millimoles) of acetyl chloride and immediately thereafter 23.7 g (300 millimoles) of pyridine were added dropwise to the thoroughly stirred solution, the temperature not rising above 5° C. during this operation. Thereafter, stirring was continued for a further 2 hours at this temperature, after which the reaction mixture was poured onto ice water. The precipitate was filtered off under suction and washed thoroughly with water. 16.9 g (97%) of crystals of melting point 166°–168° C. (ethanol) were isolated.

1-(3′-chloropropyl)-2-acetyl-9-methyl-1,2,3,4-tetrahydro-β-carboline 16.8 g (55 millimoles) of 1-(3′-chloropropyl)-2-acetyl-1,2,3,4-tetrahydro-β-carboline were dissolved in 100 ml of dimethylformamide, and 7.03 g (55 millimoles) of dimethyl sulfate were added. Thereafter, a mixture of 15 ml of dimethylformamide and 10.4 g (55 millimoles) of 30% strength sodium methylate solution was added dropwise, while cooling in an ice bath. Stirring was continued for a further 1–2 hours at 5° C., after which the mixture was poured onto 3 liters of stirred ice water. The precipitate was filtered off under suction and dissolved immediately in methylene chloride, and the solution was dried and evaporated down. The residue was purified by column chromatography (silica gel, 95:5 methylene chloride/methanol) or by recrystallization from ethanol with the addition of active carbon. 12.6 g (75%) of product of melting point 93°–95° C. were obtained.

(b) Preparation of the end product 1-(3′-dimethylaminopropyl)-2-acetyl-9-methyl-1,2,3,4-tetrahydro-β-carboline 5.5 g (18 millimoles) of 1-(3′-chloropropyl)-2-acetyl-9-methyl-1,2,3,4-tetrahydro-β-carboline were suspended in 150 ml of a 40% strength dimethylamine solution in water, and the suspension was transferred to a stirred autoclave, where it was stirred for 5 hours at 150° C. under autogenous pressure. Thereafter, the mixture was evaporated to dryness under reduced pressure, the pale oil was dissolved in methylene chloride, water was added, and the aqueous phase was brought to pH 10 with dilute sodium hydroxide solution and then extracted twice with methylene chloride. Drying and evaporating down the organic phase gave 5.8 g of crude product, which was purified by column chromatography (silica gel, mobile phase 95:5 methylene chloride/methanol) or by recrystallization from ethanol with the use of active carbon. 4.7 g (83%) of an oil was isolated. This was converted to the hydrochloride by dissolving it in ether, filtering the solution and adding a solution of HCl in ether. M.p. (hydrochloride)=108°–110° C.

The following compounds were prepared by a method similar to that described in Example 1:
2. 1-(3′-Methylaminopropyl)-2-acetyl-9-methyl-1,2,3,4-tetrahydro-β-carboline, m.p.=63°–65° C.
3. 1-(3′-Diethylaminopropyl)-2-acetyl-1,2,3,4-tetrahydro-β-carboline.0.5H$_2$O, m.p.=49°–50° C.
4. 1-(3′-Dimethylaminopropyl)-2-acetyl-1,2,3,4-tetrahydro-β-carboline.0.5H$_2$O, m.p.=148°–150° C.
5. 1-(3′-Methylaminopropyl)-2-acetyl-1,2,3,4-tetrahydro-β-carboline.0.5H$_2$O, m.p.=75°–77° C.
6. 1-(3′-Aminopropyl)-2-acetyl-1,2,3,4-tetrahydro-β-carboline, m.p.=90°–92° C.
7. 2-(3′-Dimethylaminopropyl)-2-acetyl-6-chloro-1,2,3,4-tetrahydro-β-carboline.H$_2$O, m.p.=65°–67° C.
8. 1-(3′-Methylaminopropyl)-2-acetyl-6-chloro-1,2,3,4-tetrahydro-β-carboline.H$_2$O, m.p.=86°–88° C.
9. 1-(3′-Dimethylaminopropyl)-2-acetyl-9-ethyl-1,2,3,4-tetrahydro-β-carboline.H$_2$O, m.p.=78°–80° C.
10. 1-(4′-Dimethylaminobutyl)-2-acetyl-1,2,3,4-tetrahydro-β-carboline.H$_2$O, m.p.=83°–85° C.
11. 1-(3′-Dimethylaminopropyl)-2-acetyl-6-chloro-9-methyl-1,2,3,4-tetrahydro-β-carboline, m.p.=49°–50° C.
12. 1-(4′-Dimethylaminobutyl)-2-acetyl-9-methyl-1,2,3,4-tetrahydro-β-carboline.1.5H$_2$O, m.p.=44°–45° C.

The following compounds were prepared by a method similar to that described in Example 1b, but with the reaction temperature increased to 155°–180° C. and the reaction time to 6–12 hours and using the appropriate pure amine:
13. 1-(3′-Diisopropylaminopropyl)-2-acetyl-9-methyl-1,2,3,4-tetrahydro-β-carboline.0.5HCl, m.p.=56°–58° C.
14. 1-(3′-Diisopropylaminopropyl)-2-acetyl-1,2,3,4-tetrahydro-β-carboline.0.5H$_2$O, m.p.=161°–162° C.
15. 1-[3′-(2-Butyl)-isopropylaminopropyl]-2-acetyl-9-methyl-1,2,3,4-tetrahydro-β-carboline.HCl.2H$_2$O, m.p.=98°–99° C.
16. 1-(4′-Diisopropylaminobutyl)-2-acetyl-1,2,3,4-tetrahydro-β-carboline.0.5 H$_2$O, m.p.=58°–59° C.
17. 1-(3′-Diisopropylaminopropyl)-2-acetyl-6-chloro-9-methyl-1,2,3,4-tetrahydro-β-carboline, m.p.=50°–52° C.
18. 1-[3′-(Di-2-butyl)-aminopropyl]-2-acetyl-9-methyl-1,2,3,4-tetrahydro-β-carboline, oil.
19. 1-[3′-(t.-Butyl)-aminopropyl]-2-acetyl-9-methyl-1,2,3,4-tetrahydro-β-carboline, oil.
20. 1-[3′-(t.-Butyl)-aminopropyl]-2-acetyl-1,2,3,4-tetrahydro-β-carboline, m.p.=69°–71° C.

EXAMPLE 21

1-[3′-(4-Methylpiperazin-1-yl)-propyl]-2-acetyl-1,2,3,4-tetrahydro-β-carboline.H$_2$O 10.0 g (100 millimoles) of N-methylpiperazine were added to 6.5 g (22 millimoles) of 1-(3′-chloropropyl)-2-acetyl-1,2,3,4-tetrahydro-β-carboline, and the mixture was stirred for 2 hours at 80° C. After cooling, the excess amine was distilled off under reduced pressure, the mixture was taken up in ice water, the solution was extracted with methylene chloride and the organic phase was washed thoroughly with H$_2$O, dried and evaporated down. The crude product was then purified by column chromatography (silica gel, mobile phase 95:5 mixture of methylene chloride and methanol) or by recrystallization from ethanol with the addition of active carbon. 6.1 g (74%) of product of melting point 165°–167° C. were isolated.

The following compounds were prepared by a procedure similar to that described in Example 21:
22. 1-[3′-(2-Piperidin-1-yl)-ethylaminopropyl]-2-acetyl-1,2,3,4-tetrahydro-β-carboline.H$_2$O, oil.
23. 1-[3′-(2-Morpholin-1-yl)-ethylaminopropyl]-2-acetyl-1,2,3,4-tetrahydro-β-carboline.H$_2$O, oil.
24. 1-[3′-(4-Methylpiperazin-1-yl)-propyl]-2-acetyl-9-methyl-1,2,3,4-tetrahydro-β-carboline, oil.
25. 1-[4′-(4-Methylpiperazin-1-yl)-butyl]-2-acetyl-9-methyl-1,2,3,4-tetrahydro-β-carboline.H$_2$O, oil.
26. 1-[4′-(4-Methylpiperazin-1-yl)-butyl]-2-acetyl-1,2,3,4-tetrahydro-β-carboline.0.5H$_2$O, m.p.=76°–77° C.

The following compounds were prepared by a method similar to that described in Example 21, but with the reaction temperature increased to 120°–180° C. and the reaction time to 3–24 hours:
27. 1-(3′-Isopropylaminopropyl)-2-acetyl-1,2,3,4-tetrahydro-β-carboline.H$_2$O, m.p.=100°–102° C.

28. 1-(3'-n-Butylaminopropyl)-2-acetyl-1,2,3,4-tetrahydro-β-carboline.0.5H₂O, oil.
29. 1-[3'-(2-Butyl)-aminopropyl]-2-acetyl-1,2,3,4-tetrahydro-β-carboline.0.5H₂O, oil.
30. 1-[3'-(2-Methylpropyl)-aminopropyl]-2-acetyl-1,2,3,4-tetrahydro-β-carboline.0.5H₂O, oil.
31. 1-[3'-(Di-n-butyl)-aminopropyl]-2-acetyl-1,2,3,4-tetrahydro-β-carboline.0.5H₂O, m.p.=81°–83° C.
32. 1-[3'-(Di-2-methylpropyl)-aminopropyl]-2-acetyl-1,2,3,4-tetrahydro-β-carboline, m.p.=138°–140° C.
33. 1-[3'-(Di-2-butyl)-aminopropyl]-2-acetyl-1,2,3,4-tetrahydro-β-carboline.0.5HCl, m.p.=139°–141° C.
34. 1-(3'-Propylaminopropyl)-2-acetyl-1,2,3,4-tetrahydro-β-carboline.H₂O, oil.
35. 1-[3'-(Dipropyl)-aminopropyl]-2-acetyl-1,2,3,4-tetrahydro-β-carboline, m.p.=106°–108° C.
36. 2-(3'-Propylaminopropyl)-2-acetyl-9-methyl-1,2,3,4-tetrahydro-β-carboline.H₂O, oil.
37. 1-(3'-Isopropylaminopropyl)-2-acetyl-9-methyl-1,2,3,4-tetrahydro-β-carboline.H₂O, oil.
38. 1-(3'-n-Butylaminopropyl)-2-acetyl-9-methyl-1,2,3,4-tetrahydro-β-carboline.HCl.H₂O, m.p.=79°–81° C.
39. 1-[3'-(2-Butyl)-aminopropyl]-2-acetyl-9-methyl-1,2,3,4-tetrahydro-β-carboline, oil.
40. 1-(3'-Diethylaminopropyl)-2-acetyl-9-methyl-1,2,3,4-tetrahydro-β-carboline.0.5H₂O, oil.
41. 1-[3'-(Di-n-butyl)-aminopropyl]-2-acetyl-9-methyl-1,2,3,4-tetrahydro-β-carboline, oil.
42. 1-(3'-Dipropylaminopropyl)-2-acetyl-9-methyl-1,2,3,4-tetrahydro-β-carboline.HCl.1.5H₂O, m.p.=87°–89° C.
43. 1-[3'-(Di-2-methylpropyl)-aminopropyl]-2-acetyl-9-methyl-1,2,3,4-tetrahydro-β-carboline, m.p.=137°–139° C.; m.p. (hydrochloride.H₂O)=87°–89° C.
44. 1-[3'-(4-Methylpiperazin-1-yl)-propyl]-2-acetyl-9-ethyl-1,2,3,4-tetrahydro-β-carboline.0.5H₂O, m.p.=58°–61° C.
45. 1-(3'-Methylisopropylaminopropyl)-2-acetyl-9-methyl-1,2,3,4-tetrahydro-β-carboline.HCl.2H₂O, m.p.=81°–83° C.
46. 1-[3'-(Isopropyl)-aminopropyl]-2-acetyl-9-methyl-1,2,3,4-tetrahydro-β-carboline.HCl.2H₂O, m.p.=91°–93° C.
47. 1-[3'-(n-Butyl)-isopropylaminopropyl]-2-acetyl-9-methyl-1,2,3,4-tetrahydro-β-carboline.HCl.H₂O, m.p.=106°–108° C.
48. 1-[3'-(2-Methylpropyl)-isopropylaminopropyl]-2-acetyl-9-methyl-1,2,3,4-tetrahydro-β-carboline.HCl.H₂O, m.p.=128°–130° C.
49. 1-[3'-(Di-2-methylpropyl)-aminopropyl]-2-acetyl-6,9-dimethyl-1,2,3,4-tetrahydro-β-carboline, m.p.=108°–110° C.
50. 1-(3'-Dipropylaminopropyl)-2-acetyl-6,9-dimethyl-1,2,3,4-tetrahydro-β-carboline, oil.
51. 1-[3'-(Di-2-methylpropyl)-aminopropyl]-2-acetyl-6-chloro-9-methyl-1,2,3,4-tetrahydro-β-carboline, oil.
52. 1-(3'-Dipropylaminopropyl)-2-acetyl-6-chloro-9-methyl-1,2,3,4-tetrahydro-β-carboline, oil.
53. 1-(4'-Dipropylaminobutyl)-2-acetyl-9-methyl-1,2,3,4-tetrahydro-β-carboline.H₂O, oil.
54. 1-[4'-(Di-2-methylpropyl)-aminobutyl]-2-acetyl-9-methyl-1,2,3,4-tetrahydro-β-carboline.0.5H₂O, m.p.=86°–88° C.
55. 1-(4'-Dipropylaminobutyl)-2-acetyl-1,2,3,4-tetrahydro-β-carboline.0.5H₂O, oil.
56. 1-[4'-(Di-2-methylpropyl)-aminobutyl]-2-acetyl-1,2,3,4-tetrahydro-β-carboline.0.5H₂O, m.p.=126°–128° C.
57. 1-[3'-(2,6-Dimethylpiperidin-1-yl)-propyl]-2-acetyl-9-methyl-1,2,3,4-tetrahydro-β-carboline.0.5H₂O, m.p.=153°–155° C.

EXAMPLE 58

1-[3'-(4-Methylpiperazin-1-yl)-propyl]-2-acetyl-6-chloro-1,2,3,4-tetrahydro-β-carboline.0.5HCl 1.6 g (16 millimoles) of N-methylpiperazine and then 1.7 g (16 millimoles) of triethylamine were added to 5.0 g (16 millimoles) of 1-(3'-chloropropyl)-2-acetyl-6-chloro-1,2,3,4-tetrahydro-β-carboline in 30 ml of dimethylformamide, and the mixture was stirred for 3 hours at 120° C., cooled and then poured onto ice water. The resulting mixture was extracted several times with methylene chloride, and the organic phase was washed thoroughly with water, dried and evaporated down. The crude product was purified by column chromatography (silica gel, mobile phase 95:5 mixture of methylene chloride and methanol) or by recrystallization from ethanol with the addition of active carbon. 4.1 g (63%) of product were isolated; decomposition temperature=80° C.

The following compounds were prepared by a method similar to that described in Example 58:
59. 1-(3'-Piperidin-1-ylpropyl)-2-acetyl-1,2,3,4-tetrahydro-β-carboline.0.5HCl, m.p.=134°–136° C.
60. 1-(3'-Morpholin-1-ylpropyl)-2-acetyl-1,2,3,4-tetrahydro-β-carboline.H₂O, m.p.=188°–190° C.
61. 1-[3'-(4-Phenylpiperazin-1-yl)-propyl]-2-acetyl-1,2,3,4-tetrahydro-β-carboline.HCl, m.p.=170°–173° C.
62. 1-(3'-(4-(2-Methoxyphenyl)-piperazin-1-yl)-propyl]-2-acetyl-1,2,3,4-tetrahydro-β-carboline.H₂O, m.p.=183°–185° C.
63. 1-[3'-(3,5-cis-Dimethylmorpholin-1-yl)-propyl]-2-acetyl-1,2,3,4-tetrahydro-β-carboline.0.5H₂O, m.p.=63°–65° C.
64. 1-[3'-(4-Methylpiperidin-1-yl)-propyl]-2-acetyl-1,2,3,4-tetrahydro-β-carboline.HCl, m.p.=84°–87° C.
65. 1-[3'-(4-β-Hydroxyethylpiperazin-1-yl)-propyl]-2-acetyl-1,2,3,4-tetrahydro-β-carboline.1.5H₂O, m.p.=62°–65° C.
66. 1-[3'-(4-Hydroxypiperidin-1-yl)-propyl]-2-acetyl-1,2,3,4-tetrahydro-β-carboline.1.5H₂O, m.p.=66°–69° C.
67. 1-[3'-(4-Hydroxy-4-phenylpiperidin-1-yl)-propyl]-2-acetyl-1,2,3,4-tetrahydro-β-carboline.H₂O, m.p.=106°–108° C.
68. 1-[3'-(3-(4-p-Methoxyphenylpiperazin-1-yl)-propyl)-aminopropyl]-2-acetyl-1,2,3,4-tetrahydro-β-carboline.0.5H₂O, decomposition point=81° C.
69. 1-[4'-(4-(2-Methoxyphenyl)-piperazin-1-yl)-butyl]-2-acetyl-1,2,3,4-tetrahydro-β-carboline.0.5H₂O, m.p.=83°–85° C.
70. 1-[4'-(4-(2-Methoxyphenyl)-piperazin-1-yl)-butyl]-2-acetyl-9-methyl-1,2,3,4-tetrahydro-β-carboline.0.5H₂O, m.p.=59°–61° C.

EXAMPLE 71

1-(3'-Piperazin-1-ylpropyl)-2-acetyl-1,2,3,4-tetrahydro-β-carboline.1.5H₂O 7.0 g (82 millimoles) of piperazine were dissolved in 70 ml of dimethylformamide at about 50° C., 5.0 g (17 millimoles) of 1-(3'-chloropropyl)-2-acetyl-1,2,3,4-tetrahydro-β-carboline were added dropwise to the thoroughly stirred solution, stirring was continued for 0.5 hour at 60° C. and the solvent was then distilled off under reduced pressure. The residue was partitioned between water and methylene chloride, and the organic phase was washed thoroughly with water, dried and evaporated down to give 5.7 g of a solid, which was purified by column chromatography (silica gel, mobile phase 95:5 mixture of methylene chloride and methanol). 2.6 g (40%) of a product of melting point 65°–67° C. were obtained.

The following compounds were prepared by methods similar to those described in Examples 1, 21 and 58:

72. 1-(3'-Dipropylaminopropyl)-2-propionyl-9-methyl-1,2,3,4-tetrahydro-β-carboline, m.p. 72°–74° C.
73. 1-[3'-(Di-2-methylpropyl)-aminopropyl]-2-propionyl-9-methyl-1,2,3,4-tetrahydro-β-carboline, m.p. 110°–112° C.
74. 1-(3'-Dipropylaminopropyl)-2-propionyl-1,2,3,4-tetrahydro-β-carboline, oil.
75. 1-[3'-(Di-2-methylpropyl)-aminopropyl]-2-propionyl-1,2,3,4-tetrahydro-β-carboline, m.p. 135°–137° C.
76. 1-[3'-(n-Butyl-2-methylpropyl)-aminopropyl]-2-acetyl-9-methyl-1,2,3,4-tetrahydro-β-carboline, m.p. 102°–104° C.
77. 1-[3'-(n-Butylisopropyl)-aminopropyl]-2-acetyl-9-methyl-1,2,3,4-tetrahydro-β-carboline, oil.
78. 1-[3-(2-Methylpropylpropyl)-aminopropyl]-2-acetyl-9-methyl-1,2,3,4-tetrahydro-β-carboline, m.p. 100°–101° C.
79. 1-[3'-(2-Methylpropylethyl)-aminopropyl]-2-acetyl-9-methyl-1,2,3,4-tetrahydro-β-carboline, m.p. 64°–65° C.

The following compounds can be prepared by methods similar to those described in Examples 1, 21 and 58:

80. 1-[3'-(Di-n-butyl)-aminopropyl]-2-propionyl-9-methyl-1,2,3,4-tetrahydro-β-carboline.
81. 1-[3'-(Di-2-butyl)-aminopropyl]-2-propionyl-1,2,3,4-tetrahydro-β-carboline.
82. 1-[3'-(Di-n-butyl)-aminopropyl]-2-propionyl-1,2,3,4-tetrahydro-β-carboline.
83. 1-(3'-Dipropylaminopropyl)-2-acetyl-6-methoxy-1,2,3,4-tetrahydro-β-carboline.
84. 1-[3'-(Di-2-methylpropyl)-aminopropyl]-2-acetyl-6-methoxy-1,2,3,4-tetrahydro-β-carboline.
85. 1-[3'-(Isopropylcyclopropyl)-aminopropyl]-2-acetyl-9-methyl-1,2,3,4-tetrahydro-β-carboline.
86. 1-(3'-Dicyclopropylaminopropyl)-2-acetyl-9-methyl-1,2,3,4-tetrahydro-β-carboline.

PHARMACEUTICAL EXAMPLE

Tablets having the following composition are produced on a tablet press in a conventional manner:
100 mg of the active compound of Example 43
150 mg of lactose
30 mg of corn starch
36 mg of cellulose
10 mg of polyvinylpyrrolidone and
4 mg of magnesium stearate.

We claim:

1. A 2-substituted 1-(3'-aminoalkyl)-1,2,3,4-tetrahydro-β-carboline of formula I:

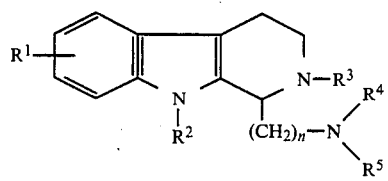

wherein n is an integer from 2 to 5, $R^1$ is hydrogen, halogen, trifluoromethyl, $C_1$–$C_4$-alkyl or $C_1$–$C_4$-alkoxy, $R^2$ is hydrogen or $C_1$–$C_3$-alkyl, $R^3$ is $C_1$–$C_3$-alkanoyl, $R^4$ is hydrogen, or an alkyl or cycloalkyl radical of not more than 4 carbon atoms and $R^5$ is hydrogen or an alkyl or cycloalkyl radical of not more than 4 carbon atoms or $R^4$ and $R^5$, together with the nitrogen atom, form a piperazine, piperidine or morpholine ring or a piperazine, piperidine or morpholine ring substituted by at least one $C_1$–$C_3$-alkyl group, and any nitrogen atom present can be substituted by $C_1$–$C_3$-alkyl, $C_1$–$C_3$-hydroxyalkyl, phenyl or by phenyl monosubstituted by methoxy or methyl, and its salts with physiologically tolerated acids.

2. 1-[3'-(Di-2-methylpropyl)-aminopropyl]-2-acetyl-9-methyl-1,2,3,4-tetrahydro-β-carboline.
3. 1-(3'-Dipropylaminopropyl)-2-acetyl-9-methyl-1,2,3,4-tetrahydro-β-carboline.
4. 1-(3'-Isopropylpropylaminopropyl)-2-acetyl-9-methyl-1,2,3,4-tetrahydro-β-carboline.
5. 1-[3'-(Di-2-butyl)-aminopropyl]-2-acetyl-1,2,3,4-tetrahydro-β-carboline.
6. 1-[3'-(Di-n-butyl)-aminopropyl]-2-acetyl-1,2,3,4-tetrahydro-β-carboline.

7. A therapeutic composition having an antiarrhythmic action, comprising: a pharmaceutical excipient and an antiarrhythmically effective amount of the compound of claim 1 as the active ingredient.

8. A method of treating cardiac arrhythmias in a patient suffering therefrom, which comprises:
administering an amount of the compound of claim 1 sufficient to exert antiarrhythmic activity in said patient.

* * * * *